United States Patent
Dey et al.

(10) Patent No.: US 6,807,796 B1
(45) Date of Patent: Oct. 26, 2004

(54) AUTOMATIC SURGICAL NEEDLE AND SUTURE LOADING MACHINE

(75) Inventors: Clifford A. Dey, Riegelsville, PA (US); Robert J. Cerwin, Pipersville, PA (US); Thomas J. Zingale, San Angelo, TX (US); Konstantin Ivanov, Basking Ridge, NJ (US); Delfin A. Lorenzo Iglesias, Guaynabo, PR (US); Manfred Hild, Schorndorf (DE); Manfred Reiser, Hertmannsweiler (DE); Bernard Wachter, Backnang (DE)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/435,769

(22) Filed: Jul. 21, 2003

(51) Int. Cl.$^7$ ............................................... B65B 63/04
(52) U.S. Cl. .......................................... 53/430; 53/116
(58) Field of Search .......................... 53/430, 116, 118, 53/58; 206/66.3, 339; 242/472.7, 613.3, 417, 476.1

(56) References Cited

U.S. PATENT DOCUMENTS

| | | | | |
|---|---|---|---|---|
| 3,541,756 A | * | 11/1970 | Mateski | ........................ 53/116 |
| 3,975,883 A | * | 8/1976 | Besnyo et al. | ................. 53/399 |
| 5,158,241 A | * | 10/1992 | Dammann et al. | ........ 242/476.7 |
| 5,174,087 A | * | 12/1992 | Bruno | ........................... 53/430 |
| 5,209,042 A | * | 5/1993 | Rickard | ........................ 53/430 |
| 5,442,896 A | * | 8/1995 | Sinn | ............................... 53/430 |
| 5,660,024 A | * | 8/1997 | Ivanov et al. | .................. 53/430 |
| 5,661,954 A | | 9/1997 | Ivanov et al. | |
| 5,664,404 A | | 9/1997 | Ivanov et al. | |
| 5,704,473 A | * | 1/1998 | Oster | .......................... 206/314 |
| 5,983,601 A | | 11/1999 | Blanch et al. | |
| 5,987,848 A | | 11/1999 | Blanch et al. | |
| 6,032,343 A | | 3/2000 | Blanch et al. | |
| 6,081,981 A | * | 7/2000 | Demarest et al. | ......... 29/407.08 |
| 6,640,734 B2 | * | 11/2003 | Hayashi et al. | ............. 112/279 |

* cited by examiner

Primary Examiner—Stephen F. Gerrity
Assistant Examiner—Paul Durand

(57) ABSTRACT

A machine and method for loading surgical needles having attached sutures into a package. The machine has a rotating disk mounted to a frame. The disk has circumferential grooves for receiving a suture. The machine has a block slidably mounted to the machine for receiving a needle and transporting it to a motion device. The motion device moves the needle to a package on a packaging machine. Rotation of the package by the packaging machine causes the suture to move out of the grooves and into the package.

14 Claims, 17 Drawing Sheets

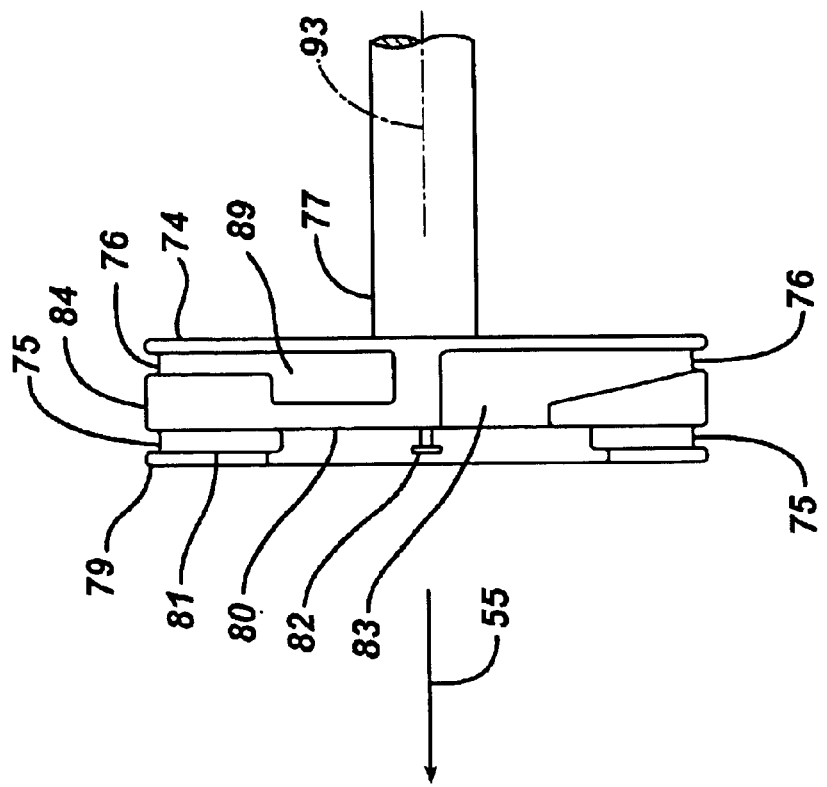
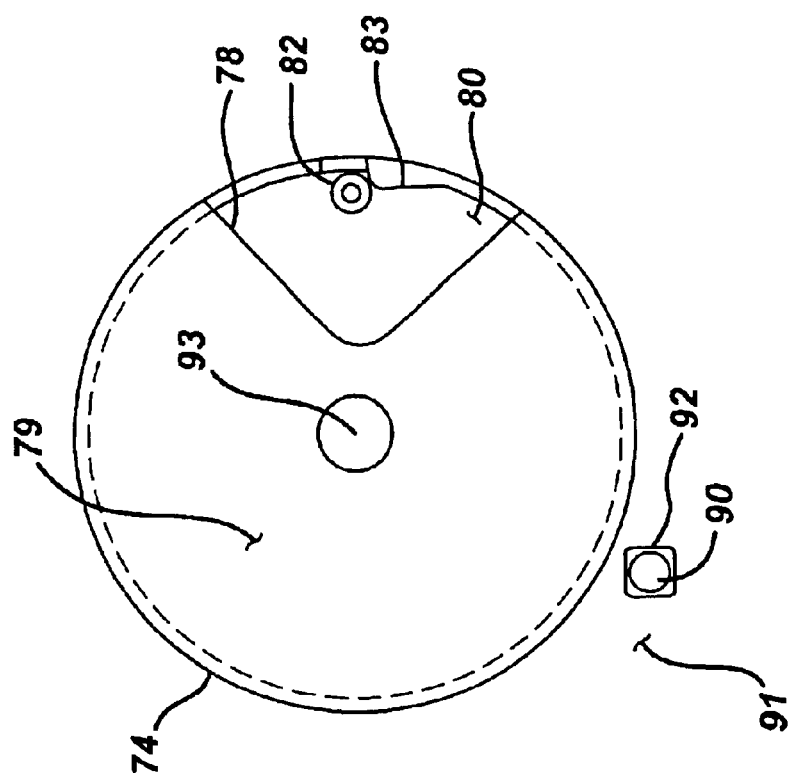
FIG. 12
FIG. 11

AUTOMATIC SURGICAL NEEDLE AND SUTURE LOADING MACHINE

TECHNICAL FIELD

The field of art to which this invention relates is machinery, more specifically, machinery for use in the manufacture, handling and packaging of surgical sutures and attached surgical needles.

BACKGROUND OF THE INVENTION

Conventional surgical sutures having conventional surgical needles mounted to one or both ends are well known in the art. The manufacture of surgical suture and needle combinations often presents challenges to the production operation with regard to the handling and transfer of the product sequentially from one operation to another. Improper handling can result in damage to the surgical suture and or needles that can substantially impair performance in the field. In particular, needles and sutures can incur damage during packaging operations, in particular automated packaging operations. Automatic machinery for packaging surgical sutures having attached surgical needles is disclosed in commonly-assigned, co-pending U.S. patent application Ser. No. 10/387,782 filed on Mar. 13, 2003, the disclosure of which is incorporated by reference.

In a typical, conventional manufacturing production process, the feeding and handling of sutures is commonly done by human workers, using their eyesight to visually choose and isolate the product from a bundle, and their fingers, hands, and arms to manually pick up the product, separate it from the bundle, and place it in the next operation. This is tedious slow work, and may tend to cause repetitive motion injury if proper work methods are not followed. The manual nature of the work imposes a production speed restriction that causes inefficiency of the downstream-mechanized packaging operation. In addition, if appropriate care is not exercised and precautions not taken, needles and sutures can be inadvertently damaged while being handled.

There is a need in this art for novel machines and methods for handling surgical sutures and attached needles in automated manufacturing and packaging processes, such that handling is minimized along with the possibility for incurring handling-created defects.

SUMMARY OF THE INVENTION

It is an object of the present invention to provide a novel machine for handling and feeding surgical suture and attached needle combinations to an automated packaging machine, wherein handling of the needle suture combination is minimized, and the needle and suture are substantially protected from handling damage.

It is yet another object of the present invention to provide such a novel machine, which also automatically places the needle in a needle park of a suture tray package, while holding and protecting the suture as it is wound into a suture channel on the package.

Accordingly, a machine for handling and feeding surgical suture and attached needle combinations is disclosed. The machine has a frame having a top surface. A rail mounted to the top surface. A block is slidably mounted to the rail; the block has a pair of jaws for receiving a surgical needle mounted thereto, and the jaws are moveable with respect to each other. A storage disk is rotatably mounted to the frame. The disk has a top, a bottom and a side. There are first and second circumferential grooves in the side of the disk for receiving at least part of a length of a suture. A passage way in the side of the disk connects the grooves. A motion device is mounted to the top surface of the machine. A pair of placement is jaws mounted to the motion device for gripping a surgical needle, the jaws are moveable with respect to each other. A displacement shaft is movably mounted to the frame, such that the shaft is displaceable between a first position and a section position, and, a displacement member is rotatably mounted to a displacement shaft for engaging a suture to move the suture between the first groove and the second groove.

Yet another aspect of the present is a novel method of handling needle and suture combinations to feed them to a packaging machine using the novel feeding and handling machine of the present invention.

These and other aspects and advantages of the present invention will become more apparent from the following description and accompanying drawings

BRIEF DESCRIPTION OF THE DRAWINGS

FIG. 11 is a plan view of the suture take-up system or storage disk of the machine of the present invention.

FIG. 12 is a side view of the suture take-up system or storage disk of FIG. 11.

DETAILED DESCRIPTION OF THE INVENTION

Figure 1:
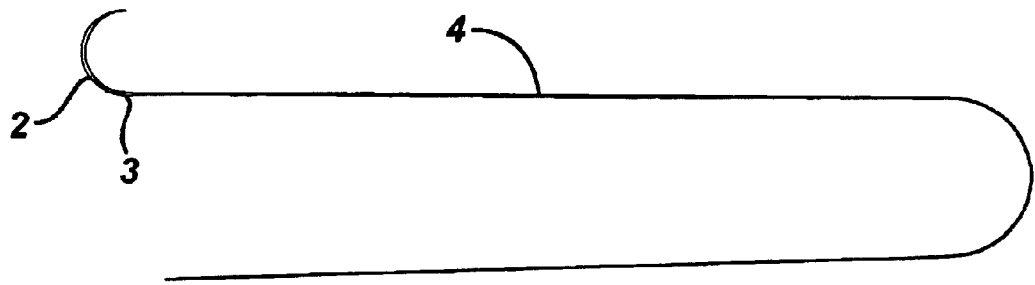
FIG. 1 is a plan view of a conventional surgical suture having a conventional surgical suture needle mounted to one end.
Figure 2:
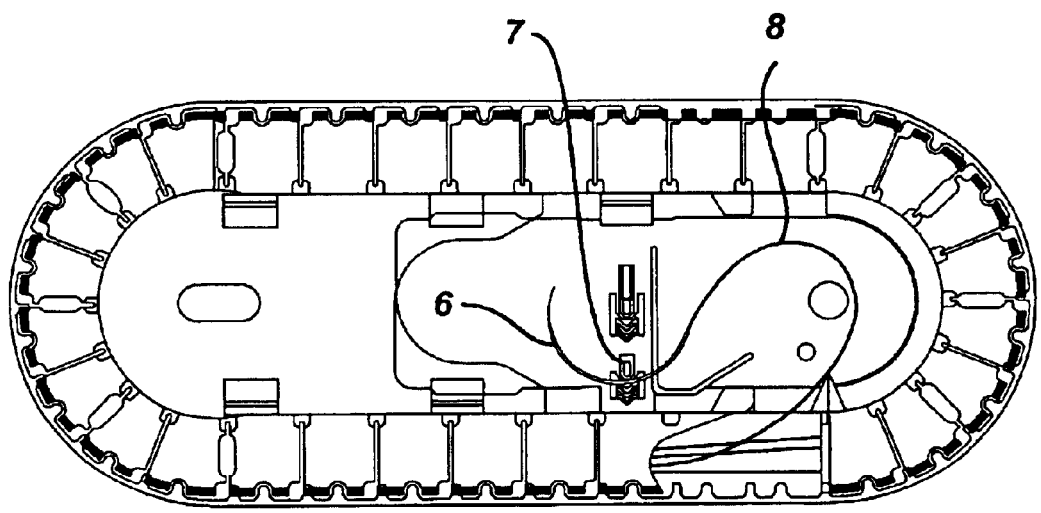
FIG. 2 is a top view of a tray package for sutures having a winding channel with the needle and suture combination of FIG. 1 mounted therein.

A typical, conventional surgical needle/suture assembly 1 is illustrated in FIG. 1. The needle 2 is seen to be attached at an attachment area 3 to a length of suture strand 4. FIG. 2 illustrates a typical, conventional tray suture package 5 having a winding channel 13. The assembly 1 is seen to be mounted in the package 5. The needle 2 is pressed into the package needle park 7 that maintains a gripping force thereon, and the suture 4 coiled in the winding channel.

Figure 3:
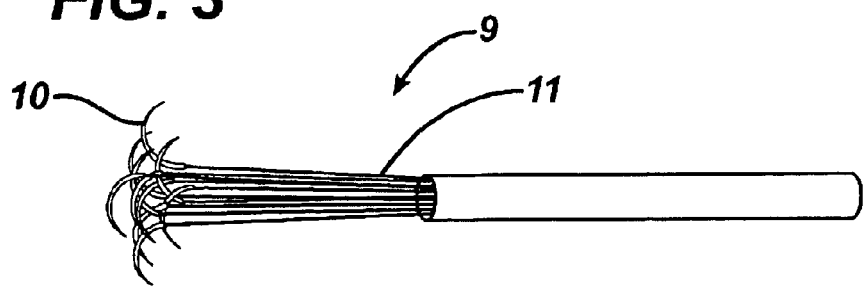
FIG. 3 is a perspective view of a bundle of surgical needle and suture assemblies.

A typical manual process that performs assembly of the package (not shown) requires the human operator of said process to select a single suture assembly 1 from a bundle 9 in a containment tube 12 (See FIG. 3), orient and position the needle 2 with fingers, withdraw the length of suture 4, manually reach into the packaging machine (not shown) and place the needle 2, into the needle park 7, pressing the needle 2 with sufficient force to deform and flex the elements of the needle park 7. The family of suture and needle assemblies that are manufactured and packaged includes small sizes for which bending damage of the needle wire is possible if sufficient care by the loading operator is not used. The family of surgical needles that may be attached to sutures also includes needle points that embody cutting edges that can cause finger injury to the operator if care is not used by the operator.

Figure 4:
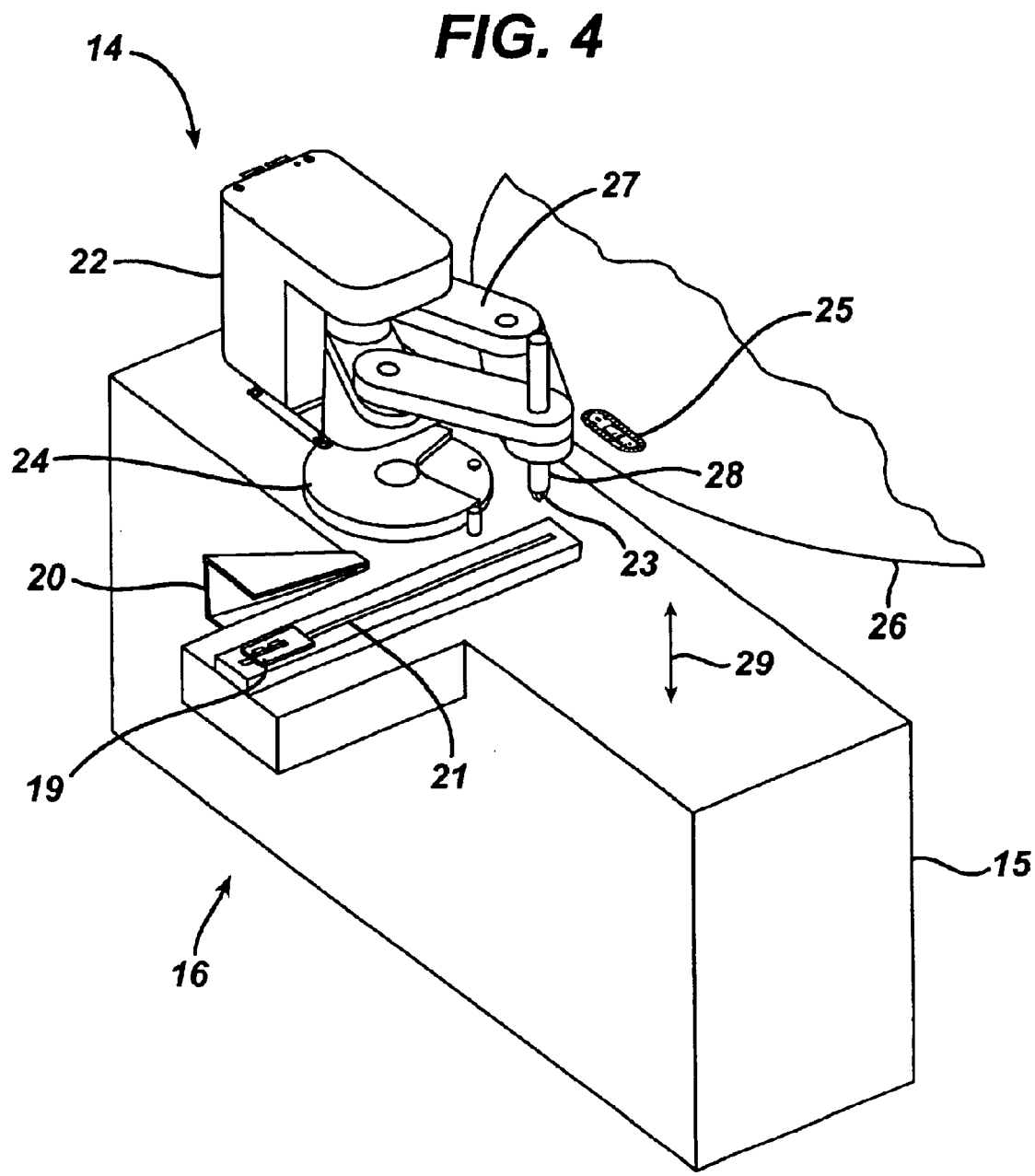
FIG. 4 is a perspective view of a loading machine of the present invention.
Figure 5:
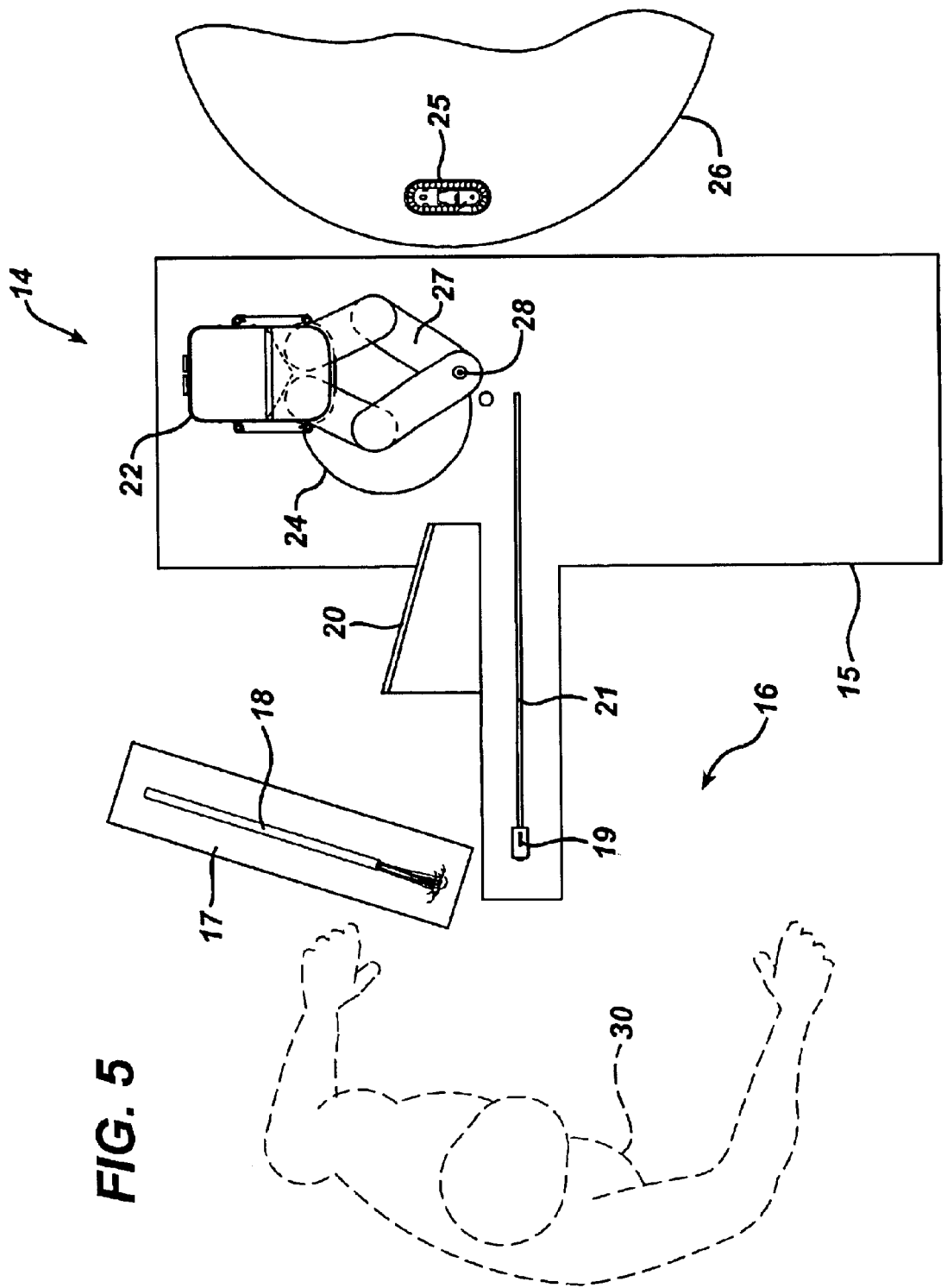
FIG. 5 is a top view of the loading machine of FIG. 4

Referring now to FIG. 4 and FIG. 5, the machine 14 of the present invention is illustrated. Machine 14 is seen to have a supporting frame and enclosure 15, operator loading area 16 having a support table 17 for the bundle of needle/sutures 9 to be loaded, needle receiving gripper 19, and suture guide funnel 20. The loading machine 14 is also seen to have a linear track 21, motion device 22, and a take-up and storage device 24. Also illustrated is a suture package 5 having a needle park 7 representing the target placement point for the needle 2. Further shown is a section of packaging machine 26 to which said loader machine 14 is attached for illustration purpose. A packaging machine, such as packaging machine 26, that is useful with the loading machine 14 of the present invention, is disclosed in co-pending, commonly-assigned U.S. patent application Ser. No. 10/387,782 filed on Mar. 13, 2003, which is incorporated by reference.

The motion device 22 is seen to have arm linkages 27 that are servo-driven to rotate and move the needle gripper jaws 23 in a prescribed path, described below. Gripper jaws 23 are mounted to a quill 28 capable of programmed vertical displacement in the direction of arrow 29. Gripper jaws 23 can also apply a force in the direction of said displacement. The motion device 22 may be any conventional motion device, including a robotic controller, and preferably a robotic controller. A robotic controller is a conventional motion device that is computer driven and has a programmable path and position generator. The motion device 22 is capable of movement in the X, Y and Z planes, as well as rotation.

The automatic loading machine 14 accomplishes the objectives described herein by mechanisms and driven members best illustrated by describing the function that takes place in a typical operating sequence. The essential function of the machine is to move a suture and needle assembly 1 by picking the needle 2 from a first point in space and placing the needle 2 at a second point in space while controlling the suture 4.

The illustrations and explanation of machine 14 contained herein do not include detailed descriptions of conventional, known motion devices such as air cylinders, powered slides, servo-driven devices, lead screws, robotic devices or robotic gripper jaws since such techniques used are within the normal ability and commercial sourcing of one skilled in the art of machine design. For the same reasons, details regarding conventional, known electronic devices such as proximity sensors, timers, shift registers, photo cells, force sensors, load cells, displacement sensors, limit switches, and demagnetizers are not included. The text will describe the function or motion of the machine without a description of the generating device, with the understanding that one skilled in the art of machine engineering would have a number of available methods of achieving said function.

Figure 6:
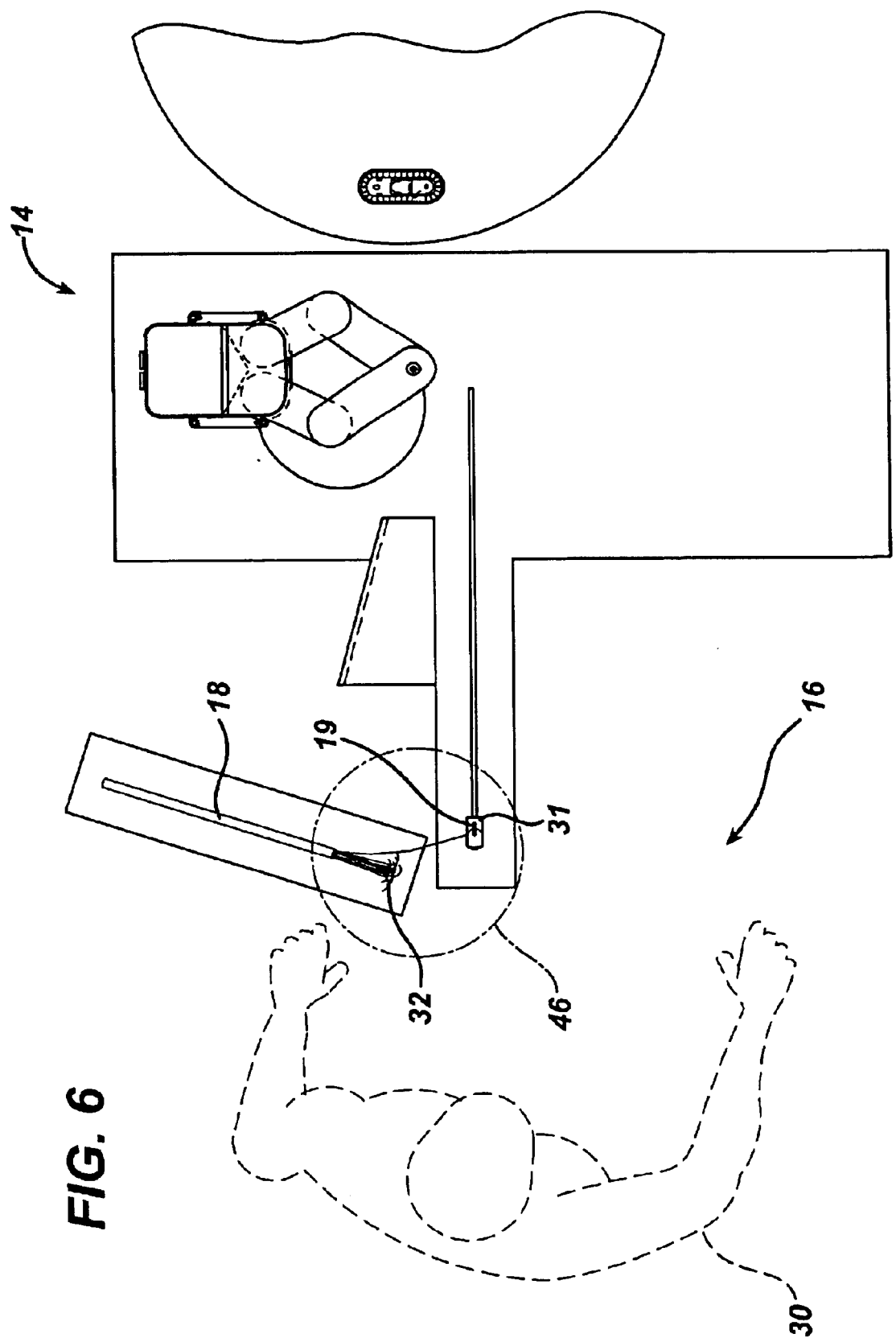
FIG. 6 is a top view of the loading machine of FIG. 5.

Referring now to FIG. 6, the automatic loading machine 14 of FIG. 5 is seen along with a loading operator 30 positioned at the loading station 16. A needle 2 with suture 4 attached is illustrated after having been manually moved by the operator 30, with short finger motion, from the bundle 9 in containment tube 12 to the gripper jaws 19.

Figure 7:
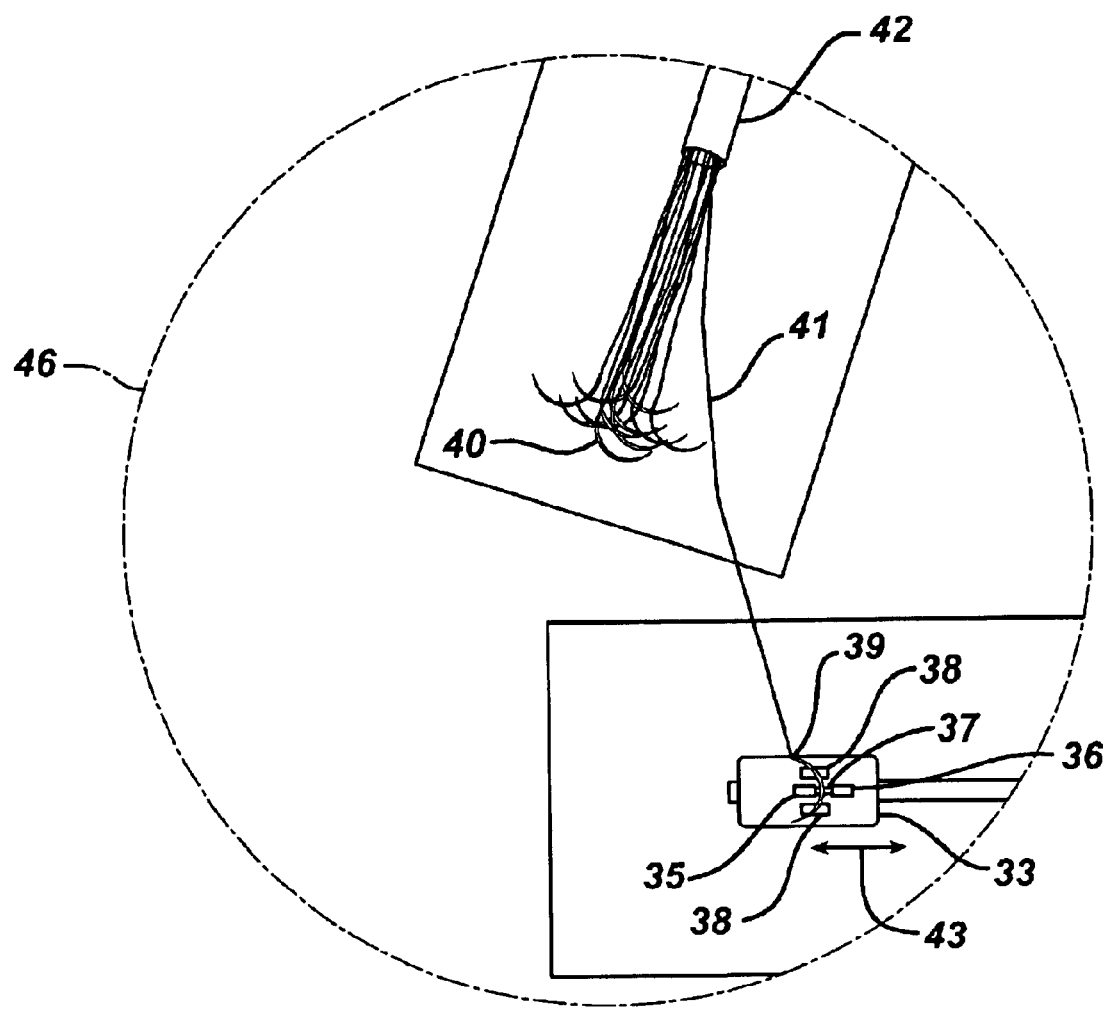
FIG. 7 illustrates a partial magnified view of the needle loading area of the machine of FIG. 6.

The dashed line 46 of FIG. 6 defines a needle loading area illustrated in the enlarged view FIG. 7. FIG. 7 illustrates the needle transfer block 33, made of non-magnetic material, slidingly mounted on the transfer track 21. Needle gripping jaws are mounted thereon including a fixed jaw 35, a moveable jaw 36, illustrated in the open position, and a gap 37 therebetween. Conventional magnets or magnetic members 38 are embedded into or mounted in or to the transfer block 33, and help to hold the needle 7 in place after the operator (not shown) has selected the needle from the bundle 9 and placed same into the gap 37. This motion withdraws a short portion of the attached suture 4 from the bundle enclosure 12. This needle loading completes the operator's task of operating the machine.

Figure 8:
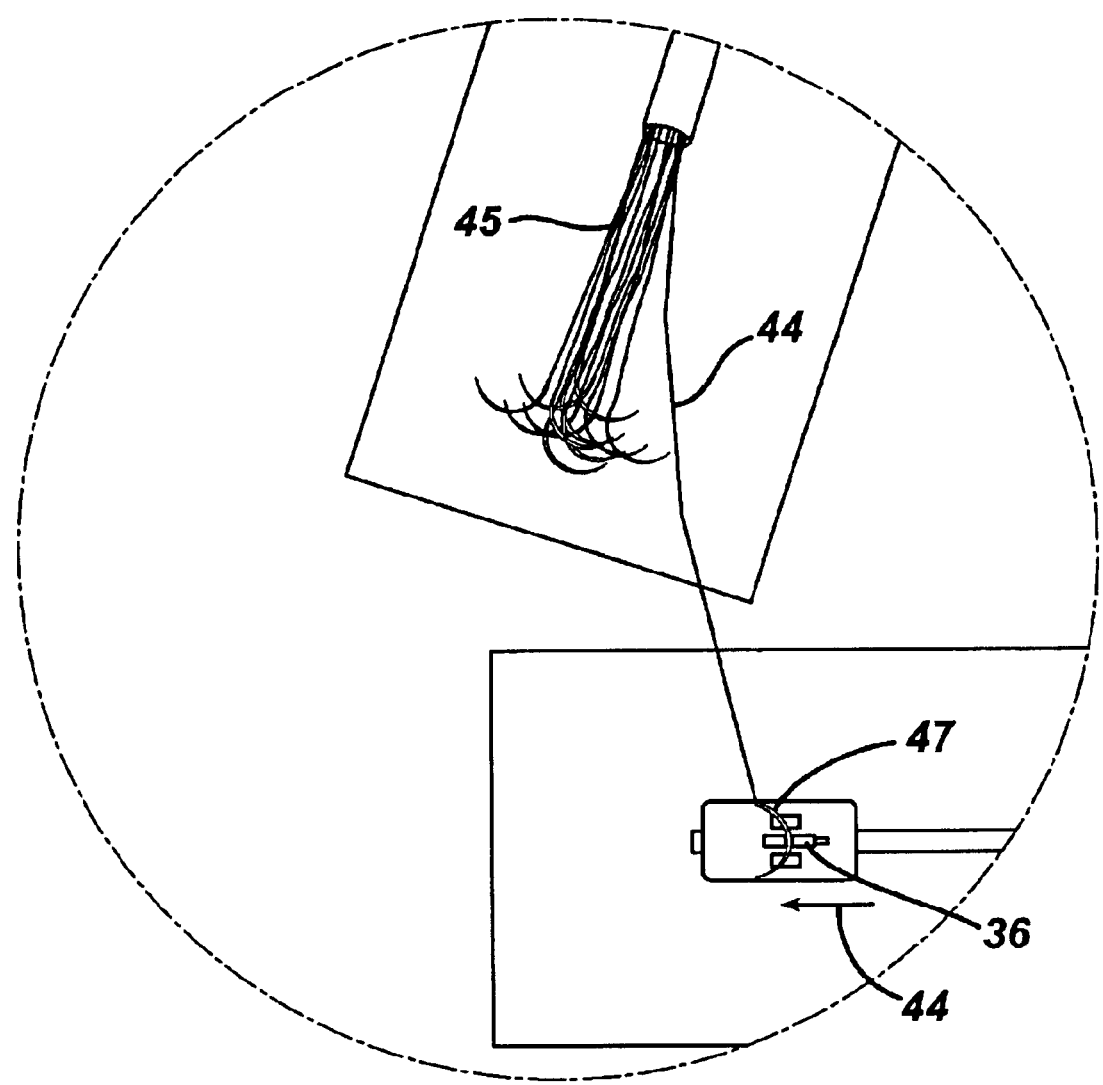
FIG. 8 illustrates the needle transfer block of the machine of FIG. 7 with the movable jaw in the closed position.

A timed signal from a conventional electronic control system (not shown) activates a conventional low force motion device such as an air cylinder (not shown) to repeatedly close and open the moveable needle gripping jaw 36 as indicated by arrow 43 on a short time sequence. If desired, although not preferred, gripping jaw 35 may also be moveable. The operator places the needle 2 in the gap 37 between said timed closures. The moveable jaw 36 closes in the direction of arrow 44 and clampingly bears on the needle 2, gripping same and providing sufficient gripping force to withstand the slight tension of withdrawing the remaining suture length from the bundle 9, illustrated in FIG. 8. A conventional displacement sensor (not shown) detects that the moveable jaw 36 has not closed completely due to the thickness of the needle wire therein. Said displacement sensor initiates an electronic signal to maintain dosing force on the jaw 36 and start the machine loading cycle. This automatic cycle initiation eliminates the need for a repetitive cycle start by the operator via hand or foot switch, and ergonomic demands thereof.

Figure 9:
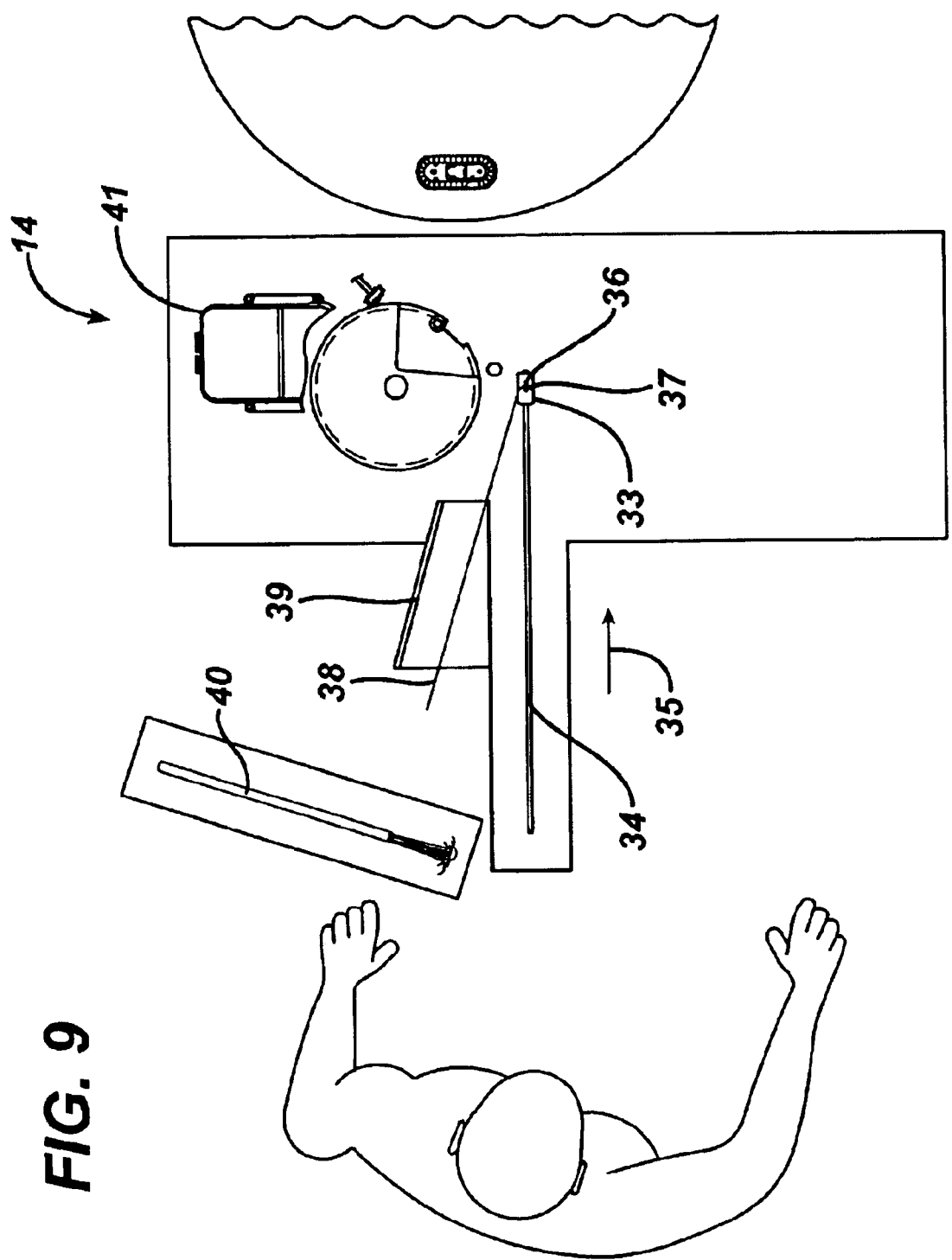
FIG. 9 illustrates the machine of FIG. 6, with the needle transfer block containing the grasped needle moved to the robotic manipulator

As seen in FIG. 9, at initiation of the machine load cycle, the transfer block 19 having gripping jaws 36 mounted thereon, is advanced on the transfer track 21 in the direction of arrow 35, thereby carrying the needle 2 accordingly. Said movement of the needle 2 withdraws the suture 4, through the guide funnel 20, from the bundle 9. For visual clarity, the motion device 22 of FIG. 9 has the arms and front portion broken away thereby allowing mechanisms therebelow to be in view.

Figure 10:
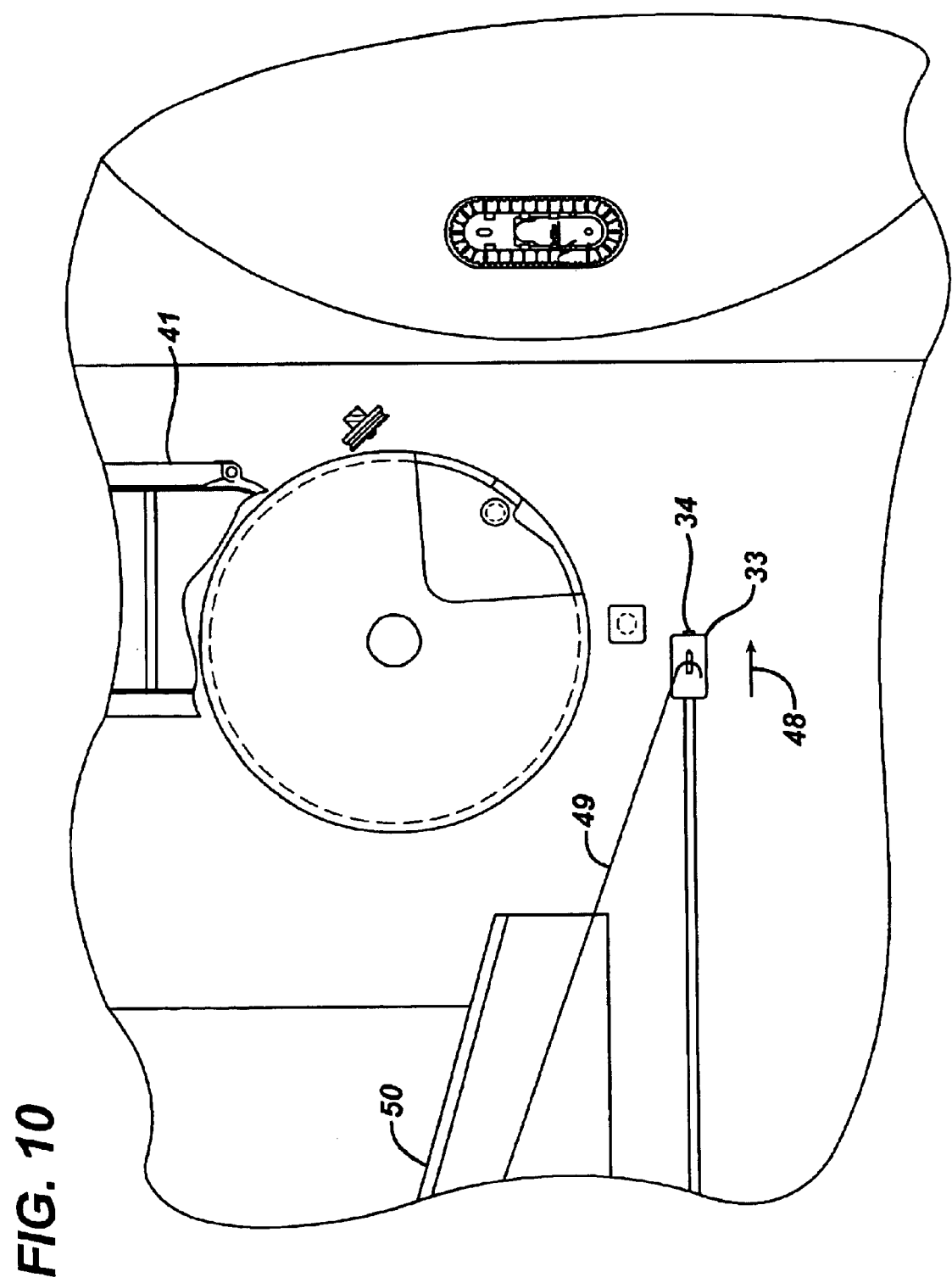
FIG. 10 is a partial magnified view of the machine of FIG. 9, with the needle transfer block proximate to the robotic manipulator.

FIG. 10 illustrates an enlarged view of the loading mechanisms of FIG. 9. The arms of the motion device 22 remain broken away for visual clarity. The transfer block 19 translates in the direction of arrow 48 to a stop position at the end of the transfer track 21. At this point of the cycle the free length of the suture 4 is free and at rest in the guide funnel 20.

Referring now to FIG. 11, a plan view of the suture take-up system is illustrated, and also referring to FIG. 12, an elevation orthogonal projection of FIG. 11 looking in the direction of arrow 55 is also illustrated. The suture take-up system is seen to have a disk 74, mounted on a driven shaft 77 rotatable about the vertical axis 93, with essentially two circumferential grooves 75 and 76 on the outer peripheral face 84 thereof. The disk 74 has a generally pie-shaped cut 78 in the face 79, parallel thereto, to a depth whereby the parallel planer surface 80 generated by the cut 78 is coplanar with the inboard wall 81 of the first groove 75. A headed pin 82 is fixedly mounted normal to said surface 80 at a location roughly central within said cut 78 and near the outer diameter of the disk 74. A milled pocket 83 forms a tapered entry to the second groove 76. A terminal pocket 89 forms the end of the second groove 76

A stationary post 90 is fixedly mounted normal to the tool plate surface 91 surrounding the wheel 74. The stationary post 90 has a pneumatically actuated damping pad 92 capable of exerting a slight gentle downward force on the suture 4 contained between the pad 92 and the machine top surface in order to impart light frictional drag, thereby creating a low tension on the suture strand 4 (see FIG. 13) threaded thereunder as said suture 4 is pulled axially. Said light tension is adjusted to be minimally sufficient to cause the suture strand 4 to stay oriented in a straight line, overcoming static electricity, air currents, or gravitational forces.

Figure 13:
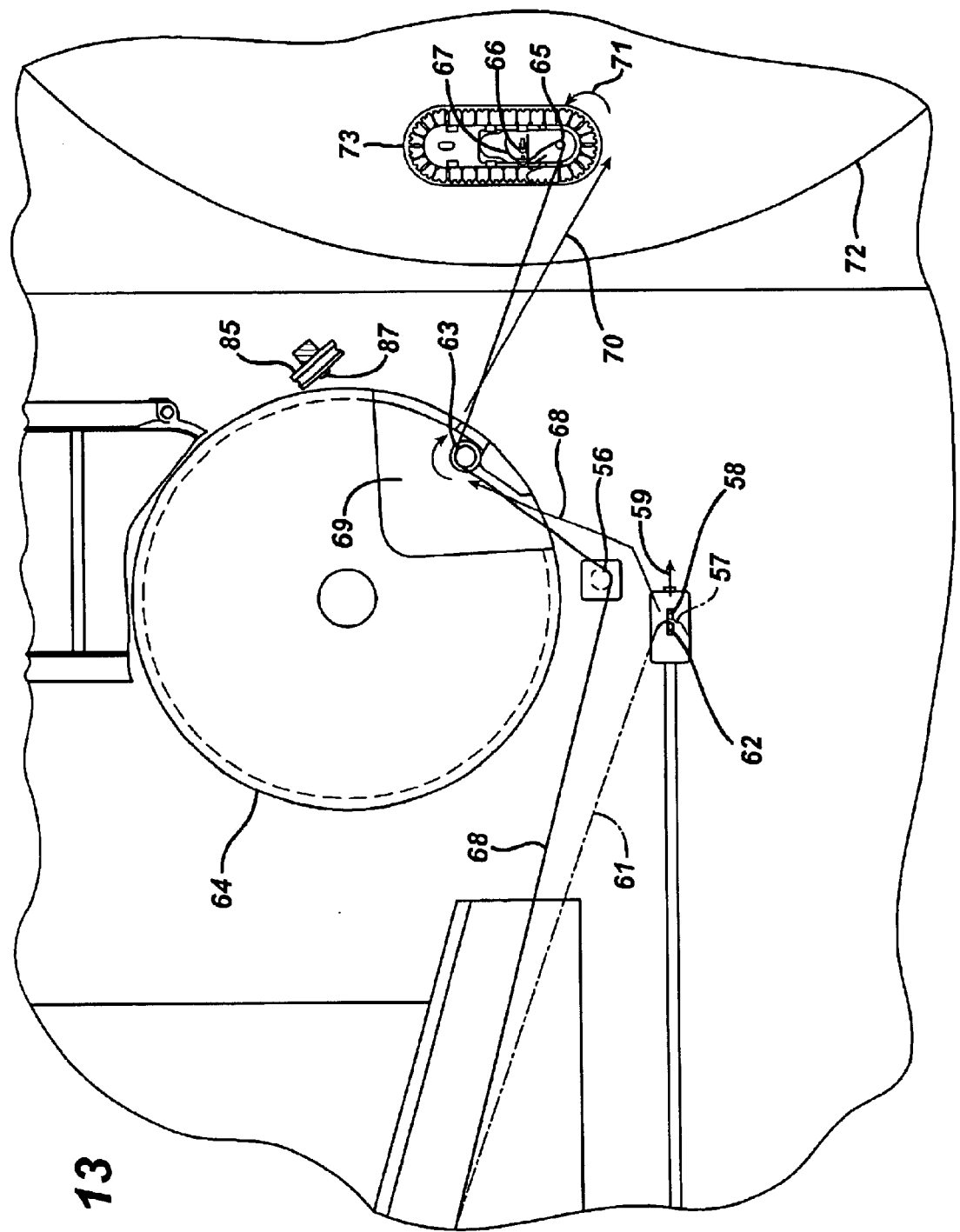
FIG. 13 is an illustration of the machine of FIG. 10 showing the movement path of the needle and suture.

FIG. 13 is an illustration of the machine of FIG. 10 illustrating the movement path of the needle 2 and suture 4. The robotic manipulator or motion device 22 accomplishes said movement. Referring also to FIG. 4, the robot arms 27 are seen to move the needle gripper jaws 23 that are fixed on the lower end of the quill 28. Said quill 28 is slidingly powered vertically and rotationally programmable to apply vertical position, rotational angle, and axial downward force. Robot arms 27 are also programmable in angle from the base 22, resulting in precise two dimensional positioning of said needle gripper jaws 23 within the field of range of said robotic manipulator 22.

Referring now to FIG. 13 utilizing the needle manipulating capability of the robot described above, the machine performs the following sequence. The needle 2 and suture 4 are shown in dashed line prior to placement by the robot, and solid line 68 and 67 respectively after placement. The needle gripping jaws 23 of the robot (not shown) are positioned above the needle 2 and descend thereon, rotationally programmed to straddle the needle 2 and grippers 35 and 36. Needle gripping jaws 23 close on the needle 2. The gripping jaw 36 in the transfer block 33 opens in the direction of arrow 59, thereby releasing the needle 2. The robot jaws 23 raise the needle 2 above the transfer block 33, translate said needle 2, thereby leading also attached suture strand 4, in the direction of arrow 68, around fixed post 90, further around the headed pin 82 of the storage disk 74 as indicated by arrow 69, across and toward the target unload position on the package 5 of the packaging machine 26. The path 70 is further programmed around the winding pin 65 of the packaging machine 26 as indicated by arrow 71, and into the package needle park 7, rotating said jaws 23 axially to align said needle 2 with said needle park 7, resulting in a final needle position 67 in said package. The robot gripper jaws 23 programmingly descend and press said needle 67 into said needle park 7 with force sufficient to spring apart the park plastic retaining devices and secure said needle 2 in accordance with said package loading feature. This precise placement function eliminates the need to perform this loading manually, thereby eliminating the need for tedious precision by a human operator, the ergonomic task of reaching into a packaging machine, the ergonomic force to press the needle into the needle park, the potential for finger injury from sharp needle points and cutting edges, and the potential damage to the needle from bending fine wire sizes when pressing into the needle park. This function is accomplished at a higher rate of speed than would be possible manually, thereby permitting higher machine cycle speeds for the packaging machine.

Figure 14:
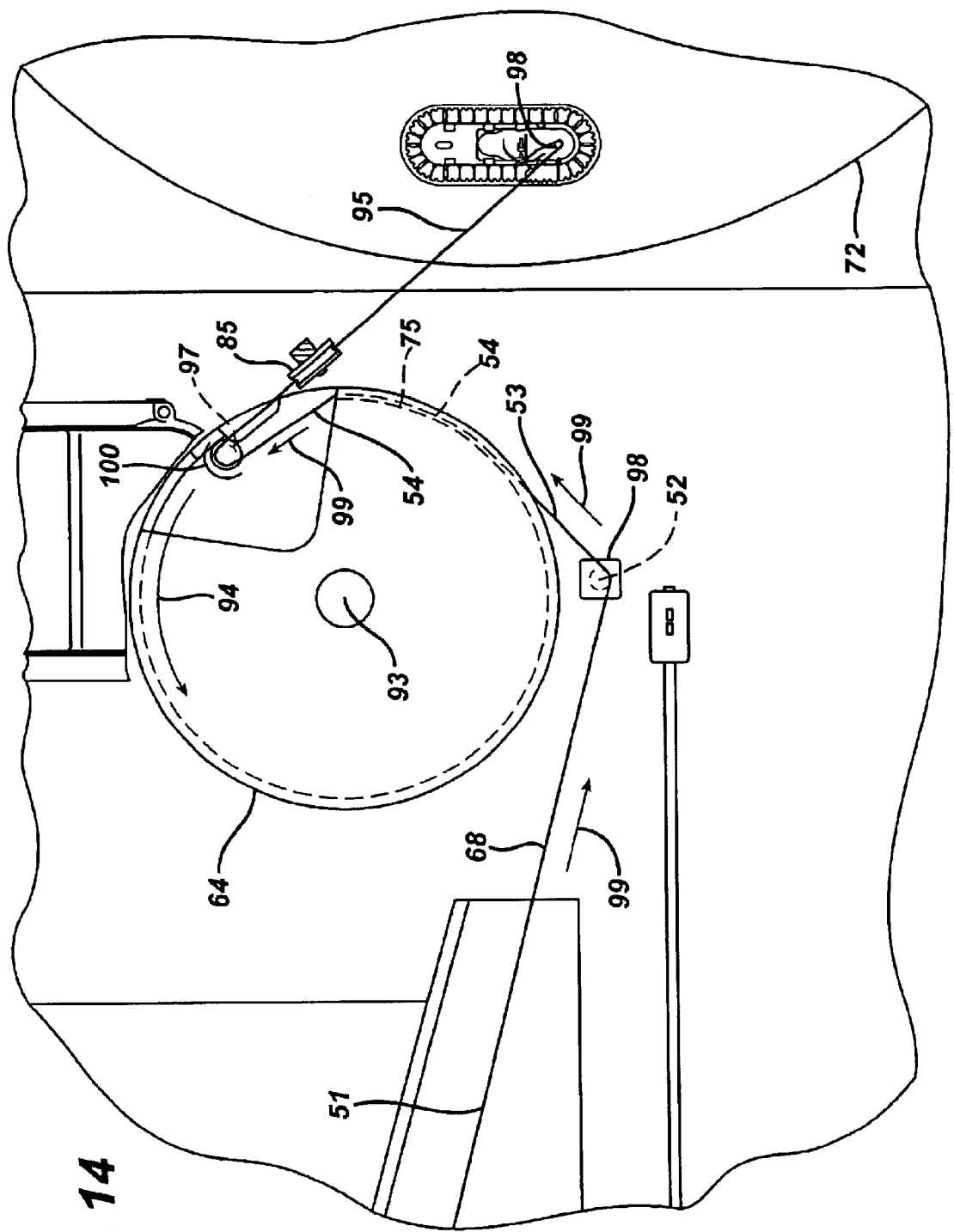
FIG. 14 illustrates the machine of FIG. 13, with the storage disk rotated to a loading position.

Continuing to refer to FIG. 13, a function of the loading machine of the present invention is to take-up, store, and protect the length of suture material 4 after withdrawing said suture length 68 from the bundle (not shown), and allow low friction dispensing therefrom as the packaging machine 26 performs its winding cycle. The features of the suture length storage system are further described by observing a functional cycle of the machine. FIG. 14 illustrates the machine of FIG. 13 whereby the storage disk 74 has been rotationally driven by a conventional servo motor or other conventional driving source (not shown) about the axis 93 in the direction of arrow 94 to an angular position that causes the suture strand 4, mildly tensioned by drag from the pressure pad 98 as said suture strand 4 is pulled to feed in the direction of arrows 99, to be aligned between the headed pin 82 and the winding pin 65, such that said suture strand 4 is under the displacement member or roller 85. The rotational driving device (not shown) for the storage disk 74 is programmed to dwell (pause in rotation) at the angular position illustrated in FIG. 14. As said rotation advances, the suture strand 4 between the stationary post 90 and the disk 74 follows in the root of the first grave 75 of said disk, slidingly advancing therein as the suture strand slides around the headed pin 82 making essentially a 180° reversing path as indicated by arrow 100. Simultaneously, the free end 51 of the suture strand 4 trails in the direction of arrow 99.

Figure 16:
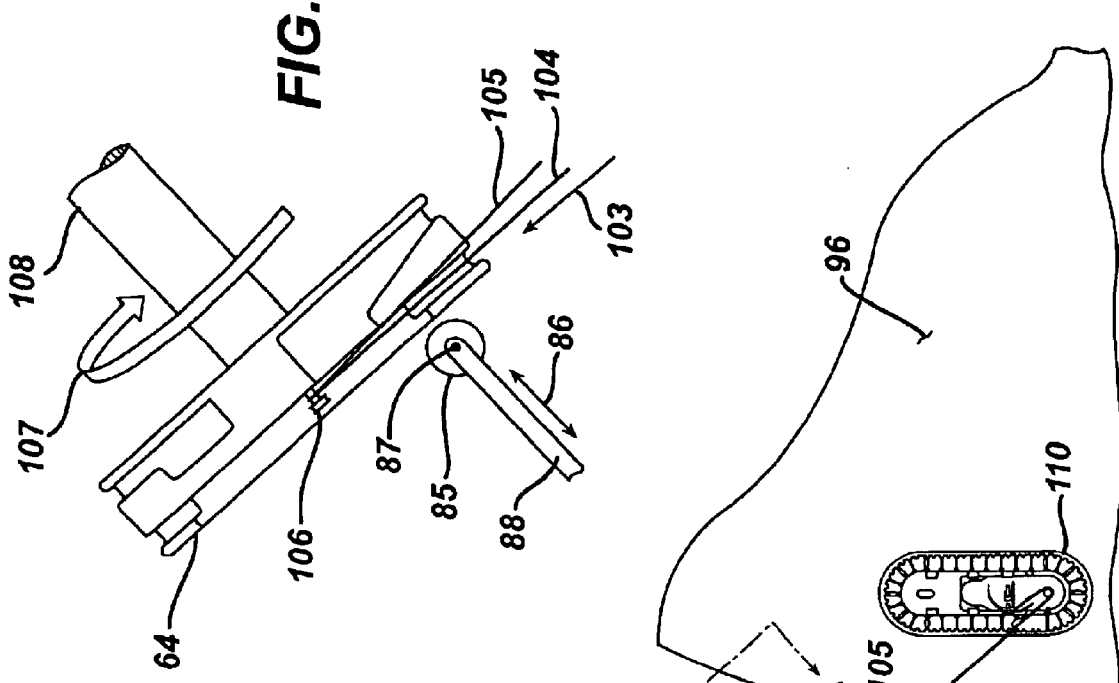
FIG. 16 is an orthogonal view of the disk storage system of FIG. 15, in the direction of arrows A—A.
Figure 15:
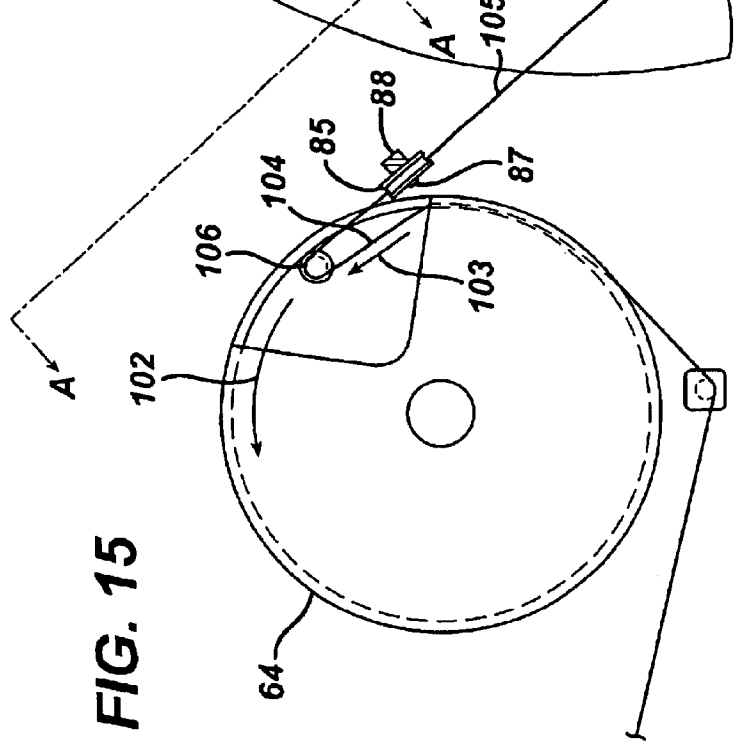
FIG. 15 is a partial view of the machine of FIG. 14, illustrating the disk storage system sequence.

Referring now to FIG. 15, the disk storage system sequence is illustrated in the plan view and an orthogonal projection view is illustrated in FIG. 16 taken accordingly by viewing from the direction indicated by arrows A—A. FIGS. 15 and 16 illustrate the machine cycle position of FIG. 14. The package 110 is illustrated on a section 96 of the packaging machine indexing turret. This combination of plan and orthogonal projections is used for FIGS. 15 through 26 to simultaneously illustrate the detail on two axes of view.

FIGS. 15 and 16 illustrate a displacement roller 85 rotatably mounted on the cantilevered pin 87 projecting from the side of the roller actuating shaft 88. The shaft 88 is displaced axially in controlled motion by a conventional actuating mechanism (not shown) that causes linear displacement as indicated by the arrow 86 when the actuation means is commanded by the control system. FIGS. 15 and 16 also illustrate the disk 74 fixed to the drive shaft 108 rotating in the direction of arrow 107 thereby causing the suture free end length 51 to move toward the headed pin 82 as indicated by arrow 103, and bend 180° therearound, while the opposite span 105 is held fixed by the package 5. The disk 74 rotation dwells in this position.

Figure 18:
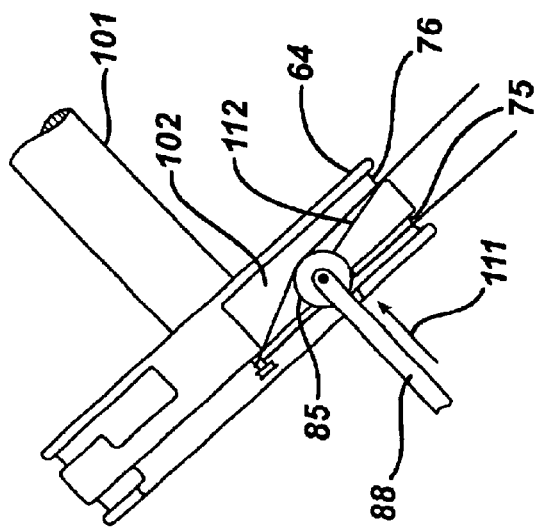
FIG. 18 is an orthogonal view of the disk storage system of FIG. 17 in the direction of arrows B—B.
Figure 17:
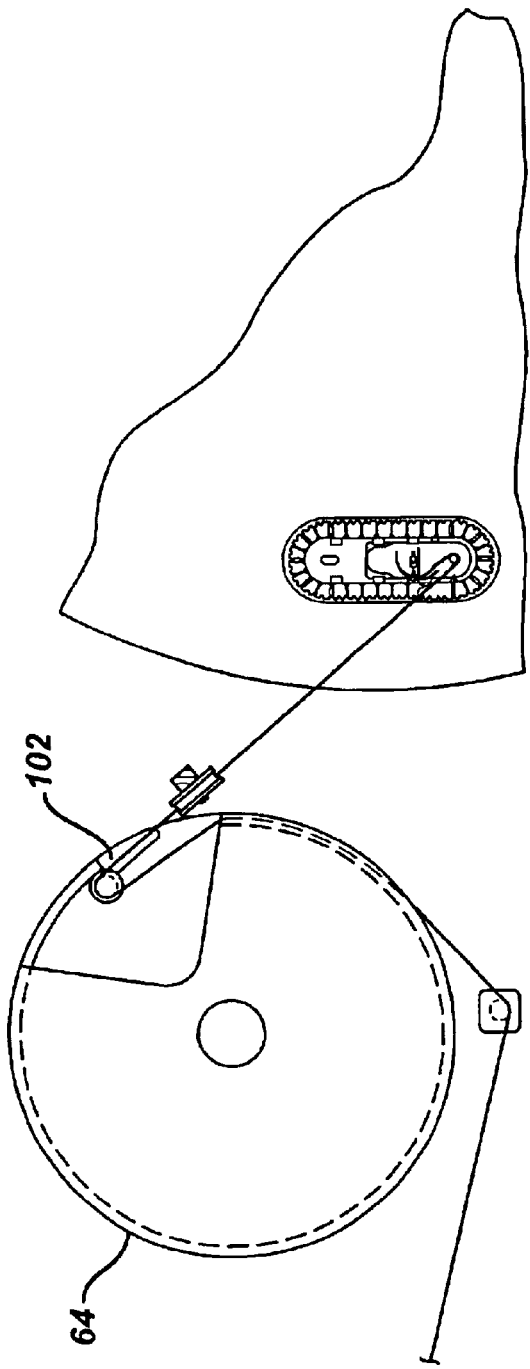
FIG. 17 illustrates the disk storage system in a dwell part of the machine cycle with the displacement roller shaft beginning the displacement function.

FIGS. 17 and 18 illustrate views similar to FIGS. 15 and 16. In this illustration the disk 64 is in a dwell (non-rotating) part of the machine cycle. Said dwell is caused by an interruption of the rotation of the disk drive shaft 101 by clutching out the drive source or programming in a conventional manner a dwell in the conventional servo motor drive (not shown). The displacement roller shaft 88 has begun the displacement function by advancing axially as indicated by arrow 111, thereby causing the displacement roller 85 to contact the suture strand 4 and displace said strand laterally. In FIG. 17 the pocket 83 in the disk 74 provides open clearance for alignment of the strand 4 to be displaced laterally from the first groove 75 toward the second groove 76 without contacting the disk 74.

Figure 20:
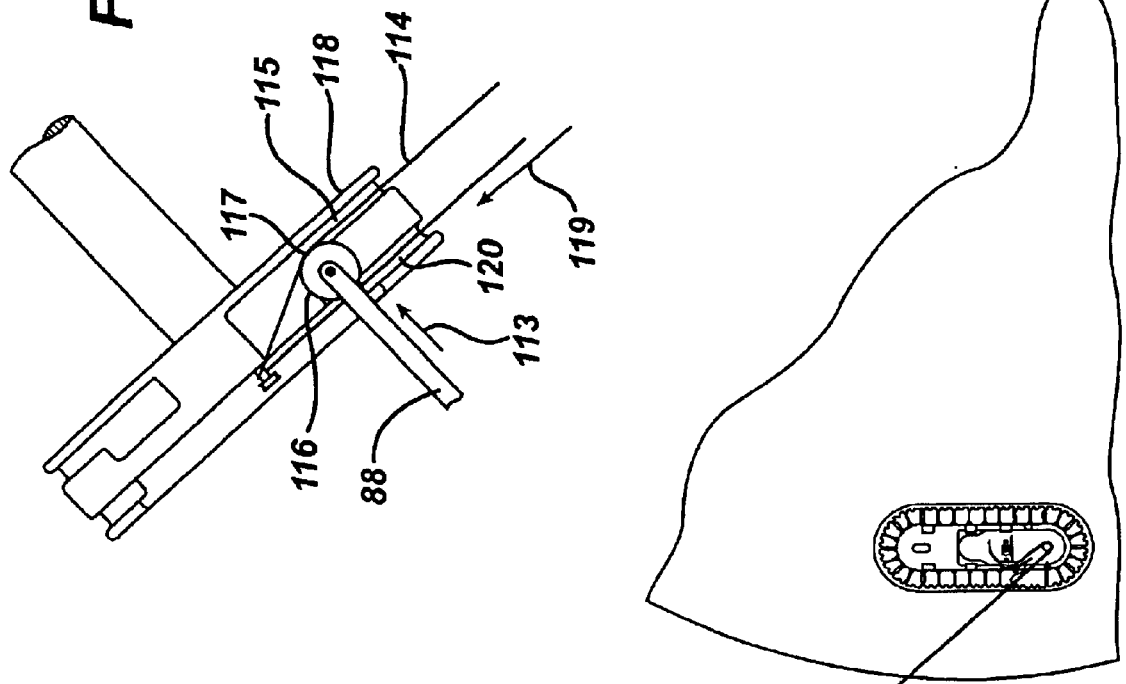
FIG. 20 is an orthogonal view of the disk storage system of FIG. 19 in the direction of arrows C—C.
Figure 19:
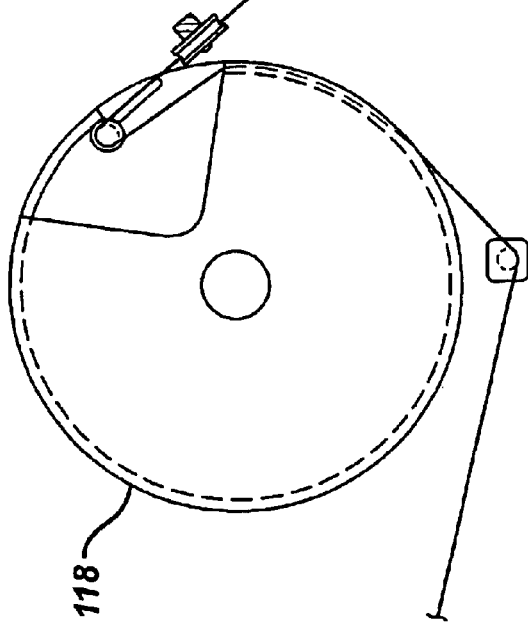
FIG. 19 illustrates the disk storage system in a dwell part of the machine cycle as the roller shaft completes its displacement stroke and the roller bears against the suture.

FIGS. 19 and 20 illustrate completion of the displacement stroke of roller 85 in the direction of arrow 113, as the disk 74 remains in a dwell (non-rotating) position. The roller 85 bears against the suture strand 4 at contact point 117, aligning said strand 4 with the second groove 76 in the disk 118. As can be seen in FIG. 20, the free end of the suture 51 remains aligned with the first groove 75 in the disk 118.

Figure 22:
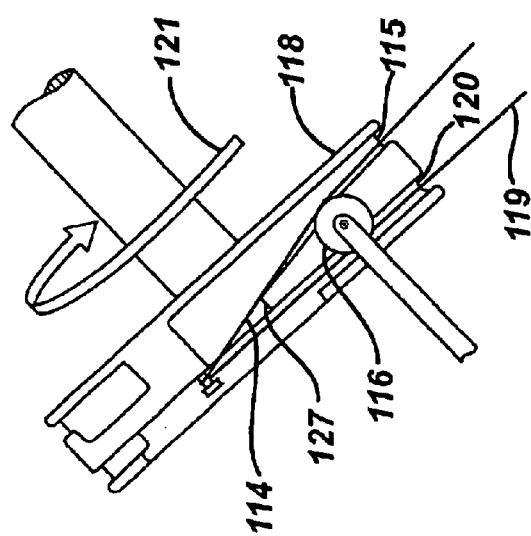
FIG. 22 is an orthogonal view of the disk storage system of FIG. 21 in the direction of arrows D—D.
Figure 21:
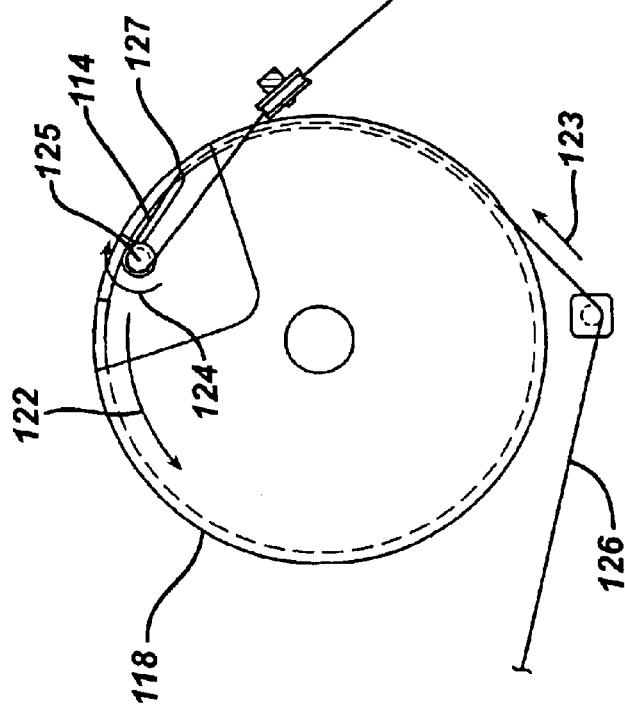
FIG. 21 illustrates the resumption of rotation of the storage disk of FIG. 19.

FIGS. 21 and 22 illustrate the resumption of rotation of the disk 74 as indicated by arrow 121 on FIG. 22. Said angular displacement moves the headed pin 82 in the direction of arrow 122, thereby causing the free section of the suture strand 51 to advance in the direction of arrow 123 and around the headed pin 82 as indicated by 180° arrow 124. Referring to FIG. 22, the continued lateral displacement of the suture strand 4 by the roller 85 causes said strand to clear the entrance wall 127 of the second groove 76 and to track therein upon continued rotation of the disk 74.

Figure 24:
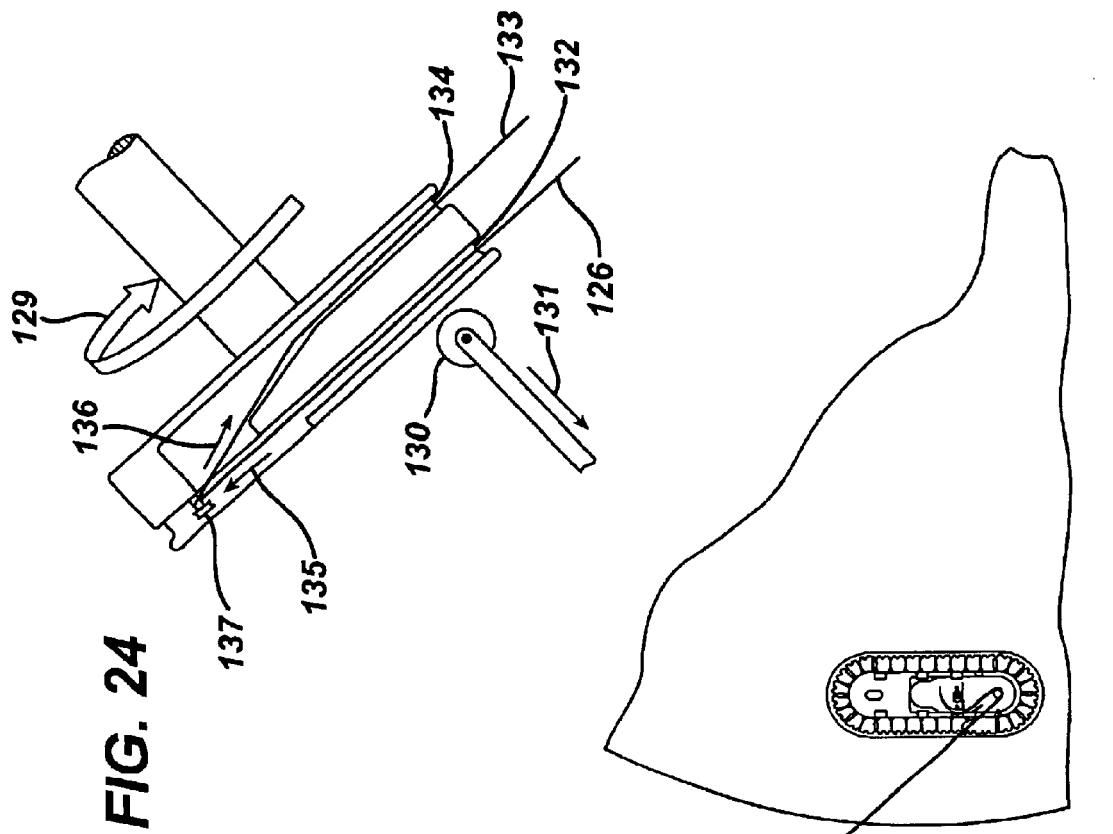
FIG. 24 is an orthogonal view of the disk storage system of FIG. 23 in the direction of arrows E—E.
Figure 23:
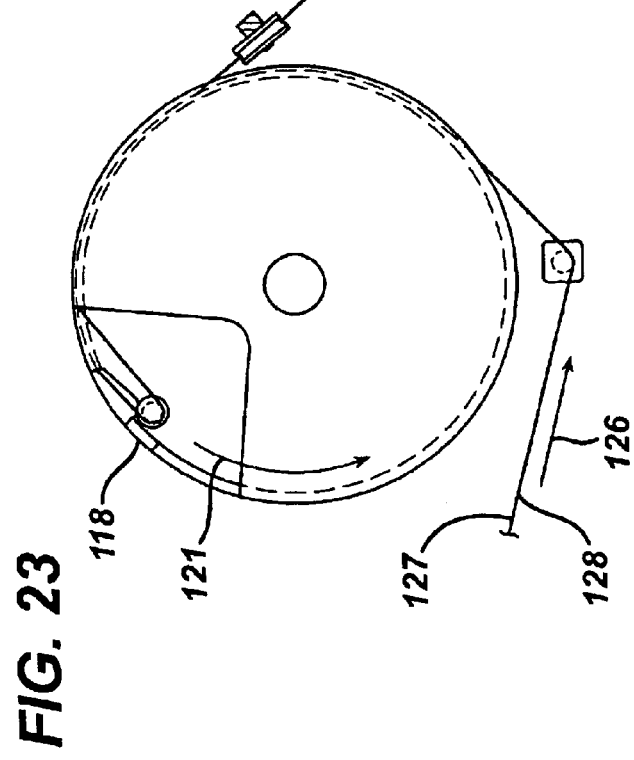
FIG. 23 illustrates the continued rotation and sequencing of the disk storage system of FIG. 21.

FIGS. 23 and 24 illustrate the continued rotation of the disk 74 as indicated by arrow 122, thereby continuing to wind the free length of suture 51 thereon. The cut end 127 of the suture strand 4 approaches the disk assembly, moving in the direction of arrow 128. FIG. 24 illustrates the disk 74 rotating as indicated by arrow 121, the displacement roller 85 withdrawn as indicated by arrow 131 to the original position indicated in FIG. 16. The free length of suture 51 is slidingly wound into the first groove 75 and the stationary length 4 slidingly into the second groove 76. Arrows 135 and 136 indicate the relative axial motion of the suture strand as the headed pin 82 advances according to the arrow 121 of FIG. 23.

Figure 26:
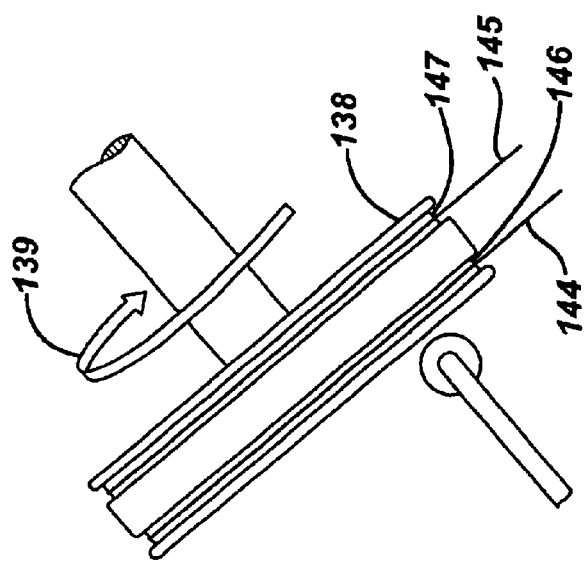
FIG. 26 is an orthogonal view of the disk storage system of FIG. 25 in the direction of arrows F—F.
Figure 25:
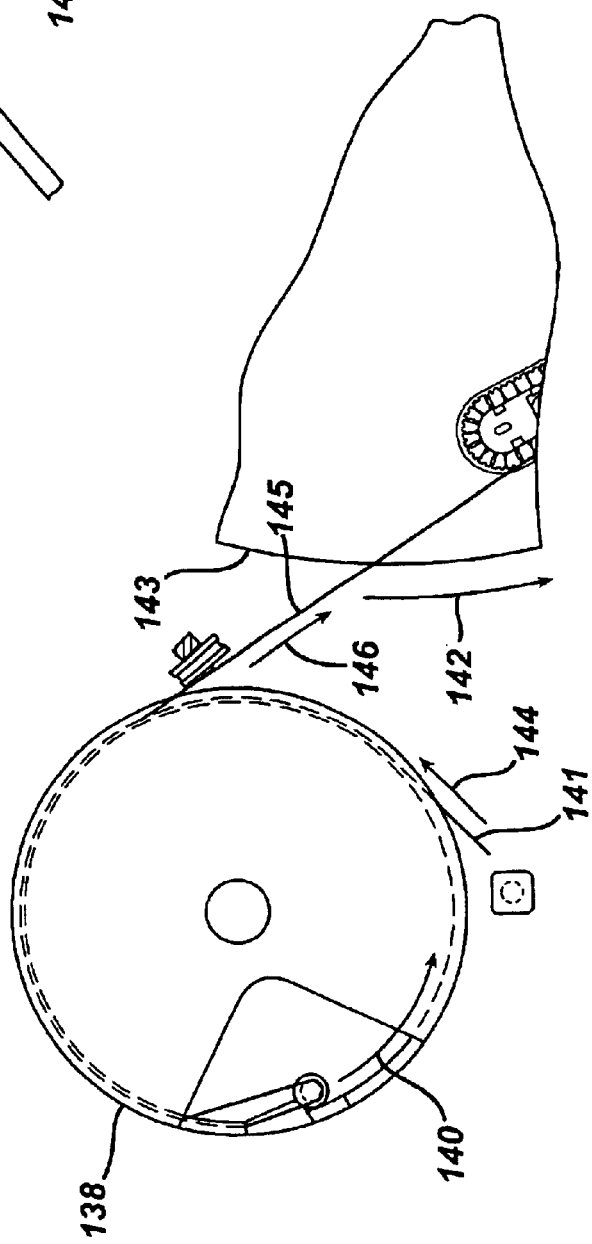
FIG. 25 illustrates the disk storage system of FIG. 23, rotated and sequenced to take up and substantially contain the suture strand in the grooves of the disk.

FIGS. 25 and 26 illustrate the continued rotation of disk 74 to take-up and contain the suture strand 4 therein. The free end 51 of the suture 4 is almost wound fully onto the disk 74, FIG. 25, as said disk rotates as indicated by arrow 140. FIG. 26 illustrates the suture strand 4 and free end 51 wound into the first groove 75 and second groove 76 respectively. FIG. 25 illustrates the packaging machine cycle pulling the suture 4 in the direction of arrow 146 as the machine turret 143 rotates as indicated by arrow 142. At any point of the disk storage system cycle, illustrated from FIGS. 16 through 26, the downstream packaging process can draw the suture 4 from the storage disk system, i.e., by rotating the suture package 5 such that the suture 4 is wound into the suture channel, and thereby causing said suture 4 to slidingly dispense free from said disk 74.

From the position of the disk 74 illustrated in FIG. 25, said disk 138 continues counterclockwise rotation to the original position of FIG. 13, for the next machine cycle. Before the next suture is threaded into the system as indicated in FIG. 13, the packaging machine 26 will have withdrawn the previous suture strand 4 sufficiently to avoid having both suture strands in the storage disk 74 at the same time (e.g., as previously mentioned, by causing the suture package 5 to rotate on the packaging machine 26 and winding the suture 4 into the suture channel 13 of the package 5). It can be seen that the storage capacity of the disk system described herein is roughly twice the circumference of said disk 74.

The novel insertion machine and method of the present invention have many advantages. Human (operator) fatigue is reduced and the production speed or rate is maximized by permitting the operator to do the minimum, low-effort step of picking a needle from a random bundle and placing into an open target area that requires minimal dependency on keen eyesight and precision of placement. In addition, the machines of the present invention automatically withdraw the entire suture length, thereby eliminating sweeping arm movements and long reaches by the operator that are ergonomically fatiguing. In addition, the cycle of the feeding machine is initiated with minimal lost time or operator effort or exposure to repetitive motion. The machine and process of the present invention also provides for gripping a needle in a way that is independent of the size or curvature, so that a mechanical tooling changeover is not required when changing product codes. In addition, the entire length of suture material is drawn smoothly from a bundle and confined in a protective device whereby the suture strand is confined in an isolated chamber or groove with smooth surfaces without exposure to sharp edges or corners that could cause surface damage. Also, the length of suture material may be withdrawn from the protective device at any time of the machine cycle, thereby enabling slow, gentle mechanical motions to do said withdrawal. Another advantage of the machine and process of the present invention is the ability to precisely place the needle into the package target area or device, and gripping said needle in an area not dependent on needle wire size or curvature. The present invention provides a way to grip a needle with gripper jaws that straddle a package needle park, thereby allowing them to push the needle into the parked position without mechanical interference with the needle park components. The jaws of the machine of the present invention grip a needle with jaws that both move, closing symmetrically, so that the needle location is not affected by changes in wire diameter. Another advantage of the machines and processes of the present invention is the overlap of the timing of motions, and operation at a sufficiently high speed to keep up with a high speed package winding machine. In addition, all motions and functions are provided in such a manner that is gentle to the needle and suture, thereby minimizing product damage. The machines of the present invention also may detect loading defects, and send a signal to the machine controller if the operation is missed or not properly accomplished.

Although this invention has been shown and described with respect to detailed embodiments thereof, it will be understood by those skilled in the art that various changes in form and detail thereof may be made without departing from the spirit and scope of the claimed invention.

We claim:

1. A method of moving a suture and surgical needle assembly to a package, comprising:

providing a surgical needle and suture assembly, comprising a surgical suture having a first end and second end, and a surgical needle mounted to an end of the suture, said suture having a length;

providing a loading apparatus for loading the surgical needle into a package, the apparatus comprising:

a frame having a top surface;

a block slidably mounted to the top surface, said block having a pair of jaws for receiving a surgical needle mounted thereto, wherein said jaws are moveable with respect to each other;

a storage disk rotatably mounted to the frame, said disk having a top, a bottom and a side;

first and second circumferential grooves contained in the side of the disk for receiving at least part of a length of a suture;

a passage way in said side of said disk connecting the grooves;

a motion device mounted to the top surface;

a pair of placement jaws mounted to the motion device for gripping a surgical needle;

a displacement shaft mounted to the frame, such that the shaft is displaceable between a first position and a section position; and, a displacement member mounted to a displacement shaft for engaging a suture to move the suture between the first groove and the second groove;

inserting the surgical needle in the jaws of the block and engaging the needle with the jaws;

moving the block and engaged needle to the motion device;

rotating the storage disk to move substantially the entire length of suture into the circumferential grooves;

employing the motion device to remove the needle from the jaws and move the needle into a suture package mounted to a suture winding machine; and, rotating the package on the winding machine to move the suture from the grooves and into the package.

2. The method of claim 1 wherein the apparatus additionally comprises a magnetic member mounted in or to the block.

3. The method of claim 1 wherein the apparatus additionally comprises a friction pad moveably mounted to the top of the machine for frictionally engaging a suture.

4. The method of claim 1 wherein the apparatus additionally comprises:

a cavity in the top of the disk, adjacent to the periphery, said cavity having a bottom; and, a pin member extending up from the bottom surface of the cavity for engaging suture.

5. The method of claim 1 wherein the apparatus additionally comprises a rail mounted to the top surface, wherein the block is slidably mounted to the rail.

6. The method of claim 1 wherein the displacement member comprises a roller that is rotatably mounted to the displacement shaft.

7. The method of claim 1 wherein the motion device comprises a robotic controller.

8. An apparatus for loading surgical needles with attached surgical sutures into a package, comprising:

a frame having a top surface:

a block slidably mounted to the top surface, said block having a pair of jaws for receiving a surgical needle mounted thereto, wherein said jaws are moveable with respect to each other;

a storage disk rotatably mounted to the frame, said disk having a top, a bottom and a side;

first and second circumferential grooves contained in the side of the disk for receiving at least part of a length of a suture;

a passage way in said side of said disk connecting the grooves;

a motion device mounted to the top surface;

a pair of placement jaws mounted to the motion device for gripping a surgical needle;

a displacement shaft mounted to the frame, such that the shaft is displaceable between a first position and a section position; and, a displacement member mounted to a displacement shaft for engaging a suture to move the suture between the first groove and the second groove.

9. The apparatus of claim 8, additionally comprising a magnetic member mounted in or to the block.

10. The apparatus of claim 8, additionally comprising a friction pad moveably mounted to the top of the machine for frictionally engaging a suture.

11. The apparatus of claim 8, additionally comprising:

a cavity in the top of the disk, adjacent to the periphery, said cavity having a bottom; and, a pin member extending up from the bottom surface of the cavity for engaging suture.

12. The apparatus of claim 8 additionally comprising a rail mounted to the top surface, wherein the block is slidably mounted to the rail.

13. The apparatus of claim 8 wherein the displacement member comprises a roller that is rotatably mounted to the displacement shaft.

14. The apparatus of claim 8 the motion device comprises a robotic controller.

* * * * *

UNITED STATES PATENT AND TRADEMARK OFFICE
CERTIFICATE OF CORRECTION

PATENT NO. : 6,807,796 B1  Page 1 of 1
APPLICATION NO. : 10/435769
DATED : October 26, 2004
INVENTOR(S) : Clifford Dey et al.

It is certified that error appears in the above-identified patent and that said Letters Patent is hereby corrected as shown below:

Title Page item 22 should read

Filed: -- May 12, 2003 --

Signed and Sealed this

Eighth Day of July, 2008

JON W. DUDAS
*Director of the United States Patent and Trademark Office*